(12) United States Patent
Bombardelli

(10) Patent No.: US 9,101,604 B2
(45) Date of Patent: Aug. 11, 2015

(54) COMPOSITIONS FOR THE TREATMENT OF DISORDERS OF THE UPPER RESPIRATORY TRACT AND INFLUENZA SYNDROMES

(75) Inventor: Ezio Bombardelli, Groppello Cairoli (IT)

(73) Assignee: INDENA S.P.A., Milan (IT)

( * ) Notice: Subject to any disclaimer, the term of this patent is extended or adjusted under 35 U.S.C. 154(b) by 380 days.

(21) Appl. No.: 12/996,159

(22) PCT Filed: May 25, 2009

(86) PCT No.: PCT/EP2009/003673
§ 371 (c)(1),
(2), (4) Date: Dec. 3, 2010

(87) PCT Pub. No.: WO2009/146807
PCT Pub. Date: Dec. 10, 2009

(65) Prior Publication Data
US 2011/0135769 A1    Jun. 9, 2011

(30) Foreign Application Priority Data

Jun. 5, 2008 (IT) .................................. MI08A1029
Jun. 12, 2008 (EP) ..................................... 08425420

(51) Int. Cl.
*A61K 36/28* (2006.01)
*A61K 9/68* (2006.01)
*A61K 36/66* (2006.01)
*A61K 36/45* (2006.01)
*A61K 36/36* (2006.01)
*A61K 31/473* (2006.01)
*A61K 36/185* (2006.01)

(52) U.S. Cl.
CPC .............. *A61K 36/36* (2013.01); *A61K 31/473* (2013.01); *A61K 36/185* (2013.01); *A61K 36/28* (2013.01)

(58) Field of Classification Search
CPC ...... A61K 36/185; A61K 36/28; A61K 33/36; A61K 36/66
See application file for complete search history.

(56) References Cited

U.S. PATENT DOCUMENTS

| | | | | |
|---|---|---|---|---|
| 4,818,533 A | * | 4/1989 | Boulware et al. | 424/725 |
| 2002/0132021 A1 | * | 9/2002 | Raskin et al. | 424/773 |
| 2006/0263459 A1 | * | 11/2006 | Zhu et al. | 424/777 |
| 2007/0082074 A1 | | 4/2007 | Wang | |

FOREIGN PATENT DOCUMENTS

| | | | | |
|---|---|---|---|---|
| JP | 2000109428 A | * | 4/2000 | |
| RU | 2 098 111 | | 12/1997 | |
| WO | 01/87247 | | 11/2001 | |
| WO | WO0187247 A | * | 11/2001 | |
| WO | 2004/014404 | | 2/2004 | |
| WO | 2006/063716 | | 6/2006 | |
| WO | WO2006063716 A | * | 6/2006 | |
| WO | WO 2006063716 A1 | * | 6/2006 | |

OTHER PUBLICATIONS

Clifford et al. (2000) J. Sci. Food Agric. 80: 1118-1125.*
Khan et a. (2010) Pharmacognosy J. vol. 2 Issue 18: 65-68.*
Negi et al. (2005) Food Chemistry 92: 119-124.*
Senchira D. et al., "Year-and-a-half old, dried Echinacea Roots Retain Cytokine-Modulating capabilities in an in-vitro human older adult model of influenza vaccination" Planta Medica, vol. 72., 2006, pp. 1207-1215.

* cited by examiner

*Primary Examiner* — Chris R Tate
*Assistant Examiner* — Russell Fiebig
(74) *Attorney, Agent, or Firm* — Silvia Salvadori, P.C.

(57) ABSTRACT

The present invention relates to compositions based on benzophenanthridine alkaloids, extract of *Hippophae rhamnoides* and extract of *Echinacea angustifolia* which possess antibacterial, antiviral and anti-inflammatory activity, and are useful in the treatment of bacterial and viral infections of the upper respiratory tract, and in the treatment of influenza.

13 Claims, No Drawings

COMPOSITIONS FOR THE TREATMENT OF DISORDERS OF THE UPPER RESPIRATORY TRACT AND INFLUENZA SYNDROMES

This application is a U.S. national stage of PCT/EP2009/003673 filed on May 25, 2009 which claims priority to and the benefit of Italian Application No. MI2008A001029 filed on Jun. 5, 2008 and European Application No. 08425420.0 filed on Jun. 12, 2008, the contents of which are incorporated herein by reference.

SUMMARY OF THE INVENTION

The present invention relates to compositions based on benzophenanthridine alkaloids, extract of *Hippophae rhamnoides* and extract of *Echinacea angustifolia*, which possess antibacterial, antiviral and anti-inflammatory activity and are useful in the treatment of bacterial and viral infections of the upper respiratory tract, and in the treatment of influenza.

PRIOR ART

The preventive and curative treatment of influenza is an important target, because this illness affects millions of people all over the world every year, with a huge loss of working hours and serious complications which, in debilitated patients, elderly people and small children, can even be fatal.

Influenza is particularly dangerous in elderly patients because of its complications, especially if they already suffer from the respiratory disorders typical of old age. The same problem arises in infants, in whom influenza leaves an aftermath of continual colds and relapses. For many years, preventive vaccination was considered to be the most effective method of dealing with viral diseases. However, in the case of influenza, the efficacy of this measure is limited due to the unusual antigen mutations caused by the appearance of new, resistant variants of the virus.

For this reason, chemotherapy and chemoprevention of viral infections are the gold standard today. Various products for the treatment of influenza exist, ranging from the old-fashioned adamantanes introduced in the 1960s to the recent neuraminidase inhibitors which, however, present low efficacy and often problems of toxicity, and cause the development of viral resistance. These substances have different impacts on strains A and B, so substances which attack both strains are essential when the type of infection is not known a priori.

Flushing, inflammation and bacterial and/or fungal infection of the throat, with formation of plaques, are common symptoms that accompany common influenza, colds and similar disorders. The common cold and influenza, which affect both children and adults up to three times a year on average, are mainly associated with viral infections, 40% of which are caused by rhinovirus, 10% by coronavirus, and a smaller proportion by adenovirus and parainfluenza virus. Although there is no specific treatment for these disorders, antihistamines, decongestants and anti-inflammatories are considered useful because reduction of oedema alleviates pain and shortens the length of the disorder underlying the inflammation.

These disorders sometimes involve complications due to the onset of secondary bacterial infections, because the outlets of the nasal sinuses are often obstructed by congestion of the mucous membranes where pathogenic germs can easily proliferate, causing fever and localised pain. In this case, antibiotic treatment is required in addition to symptomatic treatments.

The therapeutic aids used nowadays are based on eliminating possible complications, and are represented by antibiotics, anti-inflammatories and antipyretics. However, not all the preparations currently available on the market can be used by children and pregnant women. Antibiotics, especially in infants, reduce the body's defences, leading to relapses. This means that antiviral preparations which are fairly harmless to both adult patients (including pregnant women) and children, and do not cause the development of resistant viruses, is essential. The possibility of combining products which are perfectly tolerated and act on all fronts of a disorder is therefore required by the medical profession.

It has been reported in the literature that benzophenanthridine alkaloids possess antimicrobial, antifungal, antiviral and antiangiogenetic activity. The most representative of these compounds is sanguinarine, which has mainly been used in the dental profession to date for its antibacterial and anti-inflammatory action, which is useful in inhibiting plaque and protecting the gums. Benzophenanthridine alkaloids are also characterised by an anti-inflammatory effect associated with a plurality of activities, performed at nanomolar concentrations, such as:

inhibition of NFkB, a nuclear factor involved in inflammation and in the immune response to infections;

antiangiogenetic activity: the angiogenesis process is involved in inflammation and depends on VEGF (vascular endothelial growth factor), whose effect has been demonstrated in vitro on the migration of HUVECs and in vivo on angiogenesis in different models. In vitro, sanguinarine markedly suppresses the inducement of cell migration, sprouting and cell survival to a dose-dependent extent;

inhibition of 5- and 12-lipoxygenase.

These alkaloids perform a powerful synergistic action towards inflammatory processes and in bacterial and fungal infections, whereas their activity against viral infections is less marked. *Hippophae rhamnoides* extract possesses antiviral and mildly antibacterial properties.

DESCRIPTION OF THE INVENTION

The present invention relates to compositions based on:
a) benzophenanthridine alkaloids;
b) extract of *Hippophae rhamnoides;*
c) lipophilic extract of *Echinacea angustifolia*
having antibacterial, antiviral and anti-inflammatory activity, which are useful in the treatment of influenza and disorders of the upper respiratory tract.

The compositions of the invention exert a strong antiviral activity on the most common strains of influenza viruses, together with an antibacterial action, which prevents the formation of bacterial plaques and infections of the upper respiratory tract which often result from influenza. The compositions according to the invention are particularly indicated for purulent otitis and mouth infections in general. Moreover, their anti-inflammatory action is useful to treat the fever and inflammation that normally accompany colds and influenza.

It has now surprisingly been found that the compositions of the invention possess an extremely powerful antiviral, antibacterial and anti-inflammatory activity, greater than that of the sum of the various components administered separately. Said effect may be due to a synergic action mechanism not foreseeable a priori, which takes place between the various components of the combination in question.

According to the invention, the compositions will contain the various components in the following intervals (by weight per unit dose):
a) benzophenanthridine alkaloids: from 1 to 5;
b) extract of *Hippophae rhamnoides*: from 10 to 100;
c) lipophilic extract of *Echinacea angustifolia*: from 0.2 to 2.

According to a particularly preferred aspect, the compositions in question will contain the various components within the following intervals (by weight per unit dose):
a) benzophenanthridine alkaloids: from 2 to 4;
b) extract of *Hippophae rhamnoides*: from 15 to 45;
c) lipophilic extract of *Echinacea angustifolia*: from 0.5 to 1.

According to a preferred aspect of the invention, the benzophenanthridine alkaloids will be selected from sanguinarine, chelerythrine and chelidonine, or may be present in the form of extracts containing them, including their isomeric forms. Examples of said extracts are extracts of *Sanguinaria canadensis, Macleaya cordata* or *Macleaya microcarpa*, and *Chelidonium majus*. According to a particularly preferred aspect, the benzophenanthridine alkaloids will be present in the form of a purified extract of *Macleaya cordata* having an alkaloid titre of between 75 and 100%.

According to a preferred aspect, the benzophenanthridine alkaloids will be present in a form salified with luteic acid. Said salts, which are prepared by reacting the sulphates or chlorides of the alkaloids with the sodium or potassium salt of luteic acid and subsequent crystallisation, have proved particularly effective for the purposes of this invention.

According to a preferred aspect of this invention, the extract of *Hippophae rhamnoides* will be present as extract of *Hippophae rhamnoides* obtained by extraction from the aerial parts enriched with ellagic acid derivatives. According to a particularly preferred aspect, the extract of *Hippophae rhamnoides* will have an ellagitannin titre of 90%.

The extract of *Hippophae rhamnoides* is prepared by extraction from the aerial parts with alcohols having one to three carbon atoms, variously diluted with water, preferably with a 50% v/v mixture of ethanol/water, and then concentrating the water/ethanol extract until complete elimination of the organic solvent and adding to the resulting turbid suspension a quantity of polyvinylpyrrolidone amounting to 2% of the weight of the biomass. The clear solution obtained by filtration is absorbed on polystyrene resin, and the resin is washed until the soluble substances have been completely eliminated. The active ingredient that constitutes the extract used in the present invention is recovered by washing the resin with 90% ethanol, concentrating the ethanol eluate to a small volume and drying the residue under vacuum at a temperature not exceeding 50° C.

*Hippophae rhamnoides* extract presents marked antiviral activity towards various strains of influenza A and B, and towards adenovirus, paramyxovirus, *Herpes catarrhalis* viruses, cytomegalovirus and respiratory syncytial virus. The extract also presents antibacterial activity, enhanced by the fact that the ellagic tannins complex the alkaloids, anchoring the complex with the residual hydrophilic part to the viral or bacterial proteins, thus preventing their multiplication and at the same time reducing the global toxicity of the combination.

In vitro tests have demonstrated that the compositions of the invention induce the production of interferon, and inhibit bacterial and fungal proliferation and the inflammatory and pain reaction.

According to a preferred aspect, the compositions of the invention will also contain essential oils of *Echinacea angustifolia*, or the isobutylamides contained in them, which possess a powerful anti-inflammatory and analgesic activity, as they are ligands of cannabinoids CB1 and CB2.

The compositions of the invention will be conveniently formulated in the form of tablets that dissolve slowly in the oral cavity or chewing gums that release the active components slowly, mouthwashes, gels for dispersal in the oral cavity, or the like. Said formulations can be prepared according to well-known conventional methods, such as those described in "Remington's Pharmaceutical Handbook", Mack Publishing Co., N.Y., USA, together with suitable excipients.

The invention will be illustrated in detail in the example below.

EXAMPLE 1000 mg Chewable Tablets Containing

| | |
|---|---|
| Extract of *Hippophae rhamnoides* | 20 mg |
| Freeze-dried extract of *Echinacea angustifolia* | 0.5 mg |
| Alcoholic extract of *Macleaya cordata* | 2 mg |
| Soya lecithin | 30 mg |
| Anhydrous citric acid | 5 mg |
| L-cysteine | 5 mg |
| Lactose | 200 mg |
| Mannitol | 567.5 mg |
| Methylcellulose | 40 mg |
| Glycerol palmitostearate | 50 mg |
| Soft fruit flavourings | 40 mg |
| Potassium glycyrrhizinate | 5 mg |
| Talc | 10 mg |
| Sodium bicarbonate | 25 mg |

The invention claimed is:

1. A composition for treating bacterial and viral disorders of the upper respiratory tract comprising effective amounts of:
a) one or more benzophenanthridine alkaloids;
b) an extract of *Hippophae rhamnoides*; and
c) an essential oil of *Echinacea angustifolia*,
wherein said one or more benzophenanthridine alkaloids, said extract of *Hippophae rhamnoides* and said essential oil of *Echinacea angustifolia* are in a ratio of 4-1:40-15:1-0.3.

2. The composition as claimed in claim 1, wherein
a) the one or mre benzophenanthridine alkaloids are selected from sanguinarine, chelerythrine and chelidonine; and
b) the extract of *Hippophae rhamnoides* comprises ellagic tannins.

3. The composition as claimed in claim 1, wherein:
a) said one or more said benzophenanthridine alkaloids are present from 1 to 5 weight per unit dose;
b) said extract of *Hippophae rhamnoides* is present from 10 to 100 weight per unit dose; and
c) said essential oil of *Echinacea angustifolia* is present from 0.2 to 2 weight per unit dose.

4. The composition as claimed in claim 1, wherein the one or more benzophenanthridine alkaloids comprise sanguinarine, chelerythrine and chelidonine are present and are in substantially free or salified form or in the form of an extract of *Sanguinaria canadensis, Macleaya cordata, Macleaya microcarpa,* or *Chelidonium majus.*

5. The composition as claimed in claim 4, wherein the benzophenanthridine alkaloids are present in salified form with luteic acid.

6. The composition as claimed in claim 1, wherein the extract of *Hippophae rhamnoides* is prepared by a method comprising:
   extracting aerial parts of said *Hippophae rhamnoides* with a mixture of alcohol and water.

7. The composition as claimed in claim 6, wherein the extract of *Hippophae rhamnoides* has a 90% by weight of ellagitannin content.

8. The composition as claimed in claim 1, in the form of tablets, chewing gums, mouthwashes, or gels for dispersal in the oral cavity.

9. A method of treating bacterial and viral disorders of the upper respiratory tract in a subject in need thereof, comprising orally administering an effective amount of the composition according to claim 1 to the subject.

10. The method as claimed in claim 9, wherein the bacterial and viral disorders of the upper respiratory tract are caused by influenza viruses.

11. The composition of claim 1 wherein said ratio is 4:40:1.

12. A composition for treating bacterial and viral disorders of the upper respiratory tract comprising effective amounts of:
   a) one or more benzophenanthridine alkaloids;
   b) an extract of *Hippophae rhamnoides*; and
   c) an essential oil of *Echinacea angustifolia,*
   wherein said one or more benzophenanthridine alkaloids, said extract of *Hippophae rhamnoides* and said essential oil of *Echinacea angustifolia* are in a ratio of 1:15:0.3.

13. A composition for treating bacterial and viral disorders of the upper respiratory tract comprising effective amounts of:
   a) one or more benzophenanthridine alkaloids in salified form with luteic acid;
   b) an extract of *Hippophae rhamnoides*; and
   c) an essential oil of *Echinacea angustifolia,*
   wherein said one or more benzophenanthridine alkaloids, said extract of *Hippophae rhamnoides* and said essential oil of *Echinacea angustifolia* are in a ratio of 4:40:1.

* * * * *